United States Patent
Steger et al.

(10) Patent No.: US 10,350,351 B2
(45) Date of Patent: Jul. 16, 2019

(54) MEDICAL PUMP COMPRISING A HOSE CLAMP SEATING, HOSE CLAMP AND A SYSTEM CONSISTING THEREOF

(71) Applicant: B. BRAUN MELSUNGEN AG, Melsungen (DE)

(72) Inventors: Jürgen Steger, Körle (DE); Rolf Heitmeier, Baunatal (DE); Andreas Katerkamp, Melsungen (DE); Christoph Erlen, Kassel (DE); Matthias Kramer, Melsungen (DE)

(73) Assignee: B. Braun Melsungen AG (DE)

( * ) Notice: Subject to any disclaimer, the term of this patent is extended or adjusted under 35 U.S.C. 154(b) by 17 days.

(21) Appl. No.: 15/520,732

(22) PCT Filed: Oct. 5, 2016

(86) PCT No.: PCT/EP2016/073791
§ 371 (c)(1),
(2) Date: Apr. 20, 2017

(87) PCT Pub. No.: WO2017/063930
PCT Pub. Date: Apr. 20, 2017

(65) Prior Publication Data
US 2017/0312427 A1    Nov. 2, 2017

(30) Foreign Application Priority Data

Oct. 14, 2015    (DE) .................. 10 2015 117 493

(51) Int. Cl.
*A61M 5/142*    (2006.01)
*A61M 5/168*    (2006.01)
(Continued)

(52) U.S. Cl.
CPC ........ *A61M 5/16813* (2013.01); *A61M 5/142* (2013.01); *A61M 39/281* (2013.01);
(Continued)

(58) Field of Classification Search
CPC .............. A61M 5/142; A61M 5/16813; A61M 39/281; A61M 39/284
See application file for complete search history.

(56) References Cited

U.S. PATENT DOCUMENTS

| | | | |
|---|---|---|---|
| 5,219,327 A | 6/1993 | Okada | |
| 5,437,635 A | 8/1995 | Fields et al. | |
| 6,261,262 B1 | 7/2001 | Briggs et al. | |
| 8,523,803 B1 * | 9/2013 | Favreau ................ | A61M 5/142 604/67 |
| 2005/0020978 A1 | 1/2005 | Vollenweider | |
| 2013/0253442 A1 | 9/2013 | Travis et al. | |

(Continued)

FOREIGN PATENT DOCUMENTS

| | | |
|---|---|---|
| EP | 2 583 716 | 4/2013 |
| EP | 2 716 312 | 4/2014 |

(Continued)

OTHER PUBLICATIONS

English translation of International Search Report with Written Opinion for PCT/EP2016/073791, dated Jan. 20, 2017, 10 pages.

(Continued)

*Primary Examiner* — Marina A Tietjen
*Assistant Examiner* — Paul J Gray
(74) *Attorney, Agent, or Firm* — RatnerPrestia

(57) ABSTRACT

A medical pump, in particular an infusion pump for conveying a medium, includes a seating for a hose clamp which is separate from the pump and arranged on the hose. Two clamping portions of the hose clamp which can be moved relative to each other can be transferred into a closed relative position in which they pinch off the hose arranged therebetween in such a manner that it is not possible for any medium to flow through the interior of the hose. Moreover, the clamping portions can be moved with respect to each other into an opened relative position in which the hose arranged
(Continued)

between the clamping portions is not pinched off, so that the medium is able to flow through the interior of the hose. The pump is distinguished in that a sensor is provided thereon, in particular in the seating for the hose clamp, which sensor detects at least when the hose clamp is received in the seating—whether their clamping portions are in the closed or opened relative position.

17 Claims, 11 Drawing Sheets

(51) Int. Cl.
      *A61M 39/28*      (2006.01)
      *F16K 7/04*       (2006.01)
      *F16K 37/00*      (2006.01)

(52) U.S. Cl.
      CPC ........... *A61M 39/284* (2013.01); *F16K 7/045* (2013.01); *F16K 37/0041* (2013.01); *A61M 2205/14* (2013.01); *A61M 2205/18* (2013.01); *A61M 2205/33* (2013.01); *A61M 2205/3306* (2013.01); *A61M 2205/50* (2013.01)

(56) References Cited

U.S. PATENT DOCUMENTS

| | | | |
|---|---|---|---|
| 2014/0060655 A1* | 3/2014 | Ramos | F16K 7/063 |
| | | | 137/1 |
| 2014/0216557 A1 | 8/2014 | Klewinghaus | |
| 2014/0336613 A1 | 11/2014 | Roth et al. | |

FOREIGN PATENT DOCUMENTS

| | | |
|---|---|---|
| EP | 2 780 070 | 9/2014 |
| EP | 2 921 188 | 9/2015 |
| WO | WO 2011/119425 | 9/2011 |
| WO | WO2013/072199 | 5/2013 |

OTHER PUBLICATIONS

German Search Report with English language translation for Application No. 10 2015 117 493.6, dated Jun. 15, 2016, 16 pages.

\* cited by examiner

MEDICAL PUMP COMPRISING A HOSE CLAMP SEATING, HOSE CLAMP AND A SYSTEM CONSISTING THEREOF

CROSS REFERENCE TO RELATED APPLICATIONS

This application is the U.S. national phase application of PCT International Application No. PCT/EP2016/073791 filed Oct. 5, 2016, which claims priority to German Patent Application No. DE 10 2015 117 493.6 filed Oct. 14, 2015, the contents of each application being incorporated by reference herein.

FIELD OF THE INVENTION

The present invention relates to medical pumps, in particular to a medical pump which comprises a connection for a hose, in the interior of which a medium can be conveyed by means of the pump, and which has a seating into which a hose clamp which is separate from the pump can be received or installed without using any tool.

Further, the present invention relates to a hose clamp which can be attached to a pump according to aspects of the invention and by means of which a hose attached to the pump can be pinched off such that no medium can flow through the interior of the hose.

Finally, the present invention also relates to a system comprising a pump according to aspects of the invention and a hose clamp according to aspects of the invention.

BACKGROUND OF THE INVENTION

In infusion technology, transfer systems are used for conveying medications into the body of a patient. These transfer systems achieve the transfer of medications in most cases by means of hoses or hose sets and usually have shut-off devices such as roller clamps for interrupting the delivery.

In applications with demands regarding a high dosing accuracy, infusions working solely by gravity are insufficient; this is why infusion pumps are used for administering in particular life-sustaining medications.

In an infusion pump system, precautions have to be taken to avoid—during handling a hose set attached to an infusion pump or upon opening the infusion pump for interrupting the medication delivery—any free-flow situation which is life-threatening for the patient and in which the medication is supplied to the patient in an uncontrolled manner and without any dosage particularly by gravity.

DESCRIPTION OF THE RELATED ART

On the one hand, infusion pumps are known for instance from EP 2 716 312 A1 or US 2013/0253442 A1, comprising a pump-side safety clamp which prevents the occurrence of a free-flow situation during opening of the infusion pump even with an open roller clamp.

On the other hand, infusion systems are also known for instance from EP 2 583 716 A1 or EP 2 780 070 A1, which are equipped with a so-called set-side free-flow clamp. This clamp is directly located on the disposable item, for instance on the hose or hose set, and closes said disposable item upon opening a pump flap.

It is a disadvantage of this prior art that users rely on the function of the set-side free-flow clamp and hence regularly neglect to close the roller clamp.

SUMMARY OF THE INVENTION

In order to minimize the endangerment of patients, it is thus necessary in the light of this prior art to provide both a pump-side safety clamp and a set-side free-flow clamp.

It is thus an object of the present invention to provide a medical pump and/or a hose clamp which can improve the accustomed patient safety or ensure it with less expenditure, in particular during an infusion.

A medical pump according to aspects of the invention, in particular an infusion pump for conveying a medium, comprises a seating for a hose clamp which is separate from the pump and arranged on a hose that is flexible at least in sections. Two clamping portions of the hose clamp which are movable relative to each other can be brought into a closed and an opened relative position with respect to each other. In the closed relative position, the clamping portions pinch off the hose arranged therebetween such that no medium can flow through the interior of the hose. In the opened relative position, the clamping portions do not pinch off the hose arranged therebetween, so that a medium or medication and/or a body fluid such as blood can flow through the interior of the hose.

The pump according to aspects of the invention is distinguished in that a sensor is provided thereon, in particular the seating for the hose clamp, said sensor detecting on the hose clamp provided in the seating at least whether their clamping portions are in the closed or the opened relative position.

This means that the sensor is capable of detecting at least two measured values, from which one measured value is unambiguously associated to the closed relative position of the clamping portions of the hose clamp received in the seating and the other measured value is unambiguously associated to the opened relative position of the clamping portions of the hose clamp received in the seating. If the hose clamp is not placed in the seating, the sensor detects the same measured value as in the opened relative position of the clamping portions of the hose clamp received in the seating. Optionally, the sensor could also be designed such that it detects an unambiguous third measured value if the hose clamp is not placed in the seating.

The seating for the hose clamp is designed such that the hose clamp or at least one of the two clamping portions can be installed on the pump without using a tool and can be removed from the pump in a destruction-free manner. In particular, the seating comprises undercuts where portions of the hose clamp can be clamped.

The sensor may be designed such that it is capable of sensing the closed and the opened relative position of two clamping portions, which can be swiveled relative to each other, of the hose clamp received in the seating. As an alternative or in addition, the sensor may also be designed such that it is capable of sensing the closed and the opened relative position of two clamping portions, which can be shifted relative to each other or which can be swiveled and shifted relative to each other, of the hose clamp received in the seating.

The sensor may be a tactile sensor which is responsive to a contact with the hose clamp or with a part of the hose clamp. As an alternative, the sensor may also make use of optical, electrical or magnetic effects in order to detect the closed relative position.

It is an advantage of the present invention that errors on the part of the set-side hose clamp or free-flow clamp can be detected prior to the occurrence of any endangerment of the patient and the user is able to react accordingly.

Optionally, errors can be detected which arise during the manufacturing of the hose clamp (e.g. warpage due to cooling) and/or arise when the hose clamp has been already put on the market (e.g. a mechanical overload due to incorrect operation).

In an advantageous way, hose clamps suitable for the pump according to aspects of the invention do not necessarily have to fulfil the requirement in terms of first-error security and the quality demands on a clamp according to aspects of the invention can be reduced to the level of an ordinary roller clamp. This allows to cut manufacturing costs, for instance by the waiver of tests in terms of complete tightness.

The hose clamp as a safety clamp takes substantially two positions during normal use: a closed position in which the hose is pinched off, and an opened position in which the hose is not pinched off. If both positions are explicitly detected by the sensor, a redundant verification logic is implemented in which the sensor always delivers a signal both during the closed state of the hose clamp and in the opened state of the hose clamp.

The medical pump may comprise an electronic data processing unit which detects the structural and/or functional integrity of the hose clamp received in the seating required for use of the hose clamp in that it compares the temporal actual course of the measurement carried out by the sensor during the transition of the clamping portions from the closed to the opened or from the opened to the closed relative position with a temporal target course of the measurement. If there are any deviations in this comparison between the actual dynamical behavior of the hose clamp and the expected dynamical behavior of the hose clamp, the data processing unit may issue an alarm signal.

The monitoring of the dynamical behavior of the clamping portions is advantageous, as it allows to detect gradually incipient damages on the hose clamp at an earlier point in time.

The medical pump may be provided with an actuator which is able to move the clamping portions of the hose clamp which is received in the seating from the closed to the opened and/or from the opened to the closed relative position. The actuator is in particular an element which can be moved by a stepper motor and which for opening the closed hose clamp penetrates between the clamping portions and thus increases the distance between the clamping portions. As an alternative, the actuator may act only on one of the clamping portions for opening a rocker-like or clothespin-like hose clamp. It would also be possible to build up the actuator of two elements, with one element serving for moving one of the clamping portions in one direction and the other element serving for moving the same clamping portion in the opposite direction.

The advantage of a controllable actuator is that the process of opening the hose clamp can always be carried out in the same way and hence damages due to an improper opening procedure can be better avoided.

In an advantageous way, the medical pump may comprise a pump flap which in a closed position covers the seating such that the hose clamp cannot be removed from the seating or cannot be inserted into the seating, and in an opened position releases the seating such that, the hose clamp can be removed from the seating or can be inserted into the seating.

Owing to the pump flap, the measurement of the relative position of the clamping portions of the hose clamp which is received in the seating carried out by the sensor can be protected against any external disturbance variables, allowing to ensure the quality of the measurement. Even any environmental factors damaging the hose clamp or the sensor can be shielded by the pump flap. Optionally, it is also possible to design the pump flap such that the state of the hose clamp is influenced by a motion of the pump flap. By way of example, it may be designed such that the hose clamp is opened upon closing the pump flap.

In an advantageous way, the actuator, in the closed position of the pump flap, can move the clamping portions of the hose clamp which is received in the seating from the closed to the opened and/or from the opened to the closed relative position. In this way, both the measurement carried out by the sensor and the opening and closing operation effected by the actuator can be shielded against detrimental disturbance variables.

The medical pump may also be designed such that the opened relative position of the clamping portions of the hose clamp which is received in the seating can be altered by the actuator such that a degree of openness of the interior of the hose and hence a volumetric flow of the medium flowing through the hose can be adjusted. The sensor according to aspects of the invention may also be designed such that it is capable of detecting several opened relative positions of the clamping portions of the hose clamp which is received in the seating, so that the sensor is able to detect the degree of openness of the interior of the hose and hence the volumetric flow of the medium flowing through the hose.

If the sensor is capable of sensing several opened relative positions of the clamping portions, the hose clamp according to aspects of the invention can not only meet the security function to a greater extent, but may also serve for metering the medium flowing through the hose. The improvement of the security function is due to the fact that the monitoring of several states which can be adopted by the hose clamp allows to more accurately determine the position of the clamping portions in the event of a malfunction. If the pump is provided with an actuator which is able to change the relative position of the clamping portions of the hose clamp, and if the sensor is capable of sensing said relative positions adjusted by the actuator, a metering by means of the hose clamp is possible and the pump may do without any valves or roller clamps otherwise necessary.

The sensor may be designed such that it detects the closed relative position of the two clamping portions by sensing the position of the first clamping portion. The seating is especially configured such that a second one of the two clamping portions can be fixed therein. This connection may be implemented by means of a clamping connection. The seating and the sensor may be positioned relative to each other such that the sensor delivers the signal for the closed relative position of the clamping portions only if the second clamping portion is connected to the seating, in particular in a predetermined, only possible way.

If the sensor is designed such that the closed relative position of the clamping portions is detected immediately by measuring the distance between the two clamping portions, the monitoring of the hose clamp can be implemented in an efficient way.

The pump may comprise a main body relative to which the pump flap can be moved. The seating may be provided on the main body or on the pump flap, and the first clamping portion may be movable by means of the pump flap.

The connection for the hose may be positioned below the pump flap, so that the pump flap has to be opened or closed for coupling and decoupling the hose. In particular, the pump flap may be formed such that the hose clamp located in the seating is closed by opening the pump flap and/or the hose clamp located in the seating is opened by closing the pump flap.

Due to providing a pump flap acting on the hose clamp, it can be ensured in an advantageous way that the hose clamp is inevitably closed if the hose is taken out from the pump or that a proper opening process of the pump and a removal of the hose are only possible if the process of closing the hose clamp has been performed without any complications.

Both the sensor and the seating may be arranged on the main body. As an alternative, it would also be possible to provide both on the pump flap. The sensor and the seating could also be distributed to the two pump parts (i.e. the sensor on the main body and the seating on the pump flap or the seating on the main body and the sensor on the pump flap).

The pump flap may be pivotally connected to the main body.

The sensor according to aspects of the invention may be a light sensor which is responsive to at least one of the clamping portions interrupting, changing and/or deflecting a light beam emitted from a light source arranged on the pump.

In case a light sensor or an optical sensor is used for the sensor, it is possible in an advantageous way to increase the number of the states of the hose clamp which are to be measured by refining the graduation of the value range which can be measured by the sensor. If a measurable wavelength range or illumination intensity range is divided in more than two parts, for instance, it is not only possible to detect the closed and the opened relative position of the clamping portions received in the seating, but also further intermediate positions can be detected.

As described above, a tactile sensor may be used for the sensor. The tactile, sensor is in particular responsive to the contact with the first clamping portion or with the protrusion on the first clamping portion.

If the sensor is implemented as a tactile sensor, the sensor's counterpart arranged on the hose clamp and detected by the sensor can be designed so as to be robust without having special optical characteristics or any other material properties.

A hose clamp according to aspects of the invention comprises two clamping portions which can be moved relative to each other and can be brought into a closed relative position with respect to each other in which the hose arranged between the clamping portions is pinched off such that no medium can flow through the interior of the hose, and which can be moved to an opened relative position with respect to each other in which the hose positioned between the clamping portions is not pinched off so that a medium can flow through the interior of the hose. At least one of the clamping portions can be connected to a medical pump according to aspects of the invention. A first one of the two clamping portions comprises a portion which covers an aperture provided on the second one of the clamping portions in the closed relative position of the clamping portions and at least partially releases said aperture or does not cover it in the opened relative position of the clamping portions.

In particular, the aperture is an opening or recess which is provided in the second clamping portion and through which a light beam can radiate in a first direction in the opened relative position of the clamping portions of the hose clamp which is received in a seating of a medical pump according to aspects of the invention and which in the closed relative position of the clamping portions of the hose clamp which is received in the seating is concealed by the first clamping portion such that at least in the first direction a light beam cannot radiate through the aperture or only in part.

The advantage of the hose clamp provided with an aperture is that its opening state can be determined by means of a light sensor in a contact-free manner.

As an alternative, a hose clamp according to aspects of the invention comprises two clamping portions which can be moved relative to each other and from which at least one is designed in such a manner that it can be connected to a medical pump according to the application without using any tool and in particular can be detached from a medical pump according to the application without using any tool. A latching element is provided on the hose clamp, by means of which the clamping portions of the hose clamp can be held in a closed relative position or the hose clamp can be held in a closed position. In their closed relative position, the clamping portions can pinch off a flexible hose, which is arranged between them and is flexible at least in sections, such that no medium can flow through the interior of the hose.

In addition to the latching element, a protrusion is provided on the hose clamp on a first one of the two clamping portions, said protrusion in the closed relative position protruding in such a manner toward the second of the two clamping portions that it extends up to a rear side of the second clamping portion facing away from the first clamping portion. If the hose clamp according to aspects of the invention is connected to the pump, the closed relative position of the clamping portions can be detected by means of a sensor arranged on the rear side of the second clamping portion on the medical pump.

The latching element may comprise parts from which one part is provided on the first clamping portion and the other part is provided on the second clamping portion. In the closed relative position of the clamping portions, the two parts of the latching element cooperate in particular in a form-fitting manner and thus prevent a relative movement of the two clamping portions.

If the hose clamp according to aspects of the invention is attached to a hose which is connected to a medical pump, the construction of the hose clamp according to aspects of the invention allows a simple monitoring of the state of the hose clamp. If the hose clamp is formed such that the second clamping portion is the one that can be connected to the seating of the pump, the sensor may be arranged in or on the seating of the pump, which allows an easy installation of the hose clamp in the seating.

The hose clamp may be designed such that the protrusion extends in the closed relative position through a continuous recess or a hole in the second clamping portion.

By providing a continuous recess in the second clamping portion, which is penetrated by the protrusion of the first clamping portion in the closed relative position, any warpage occurred during manufacturing of the hose clamp can be detected in an easier and more reliable way.

The clamping portions of the hose clamp according to aspects of the invention may be pivotally connected to each other by means of a hinge. As described above, the latching element may comprise two parts, with one of said parts being arranged on the first clamping portion and the second part being arranged on the second clamping portion. The parts of the latching element may each be integrally formed with the corresponding clamping portion. The parts of the latching element may each be arranged on the side of each of the two clamping portions facing away from the hinge. A hose seating, in particular a chute-shaped or groove-shaped hose seating, may be provided between the side of each clamping portion facing the latching element and facing the hinge, said hose seating having a surface where the hose to be pinched off may rest at least in sections. If the recess and the protrusion are each arranged between the hinge and the respective hose seating of the corresponding clamping element, the protrusion and the latching means allow to monitor the integrity of the hinge.

If the hose is placed in the hose seatings of the hose clamp and the clamping portions are moved toward each other to such an extent that the parts of the latching elements lock in place in each other, a user can perceive said locking process owing to the resulting locking noise. If the sensor of the medical pump determines that the protrusion does not enter the recess so far as it was to be expected in the closed relative position of the clamping portions, a production error of the hinge or a damage on the hinge can be diagnosed.

A medical system according to aspects of the invention comprises a medical pump according to at least one of the aspects described above and a hose clamp according to at least one of the aspects described above.

The advantage of the system according to aspects of the invention is that—following the metered administering of a medium by means of the pump to a patient and having shut down the pump—it can be ensured without any great effort that the hose clamp is closed and that there is no free-flow situation.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
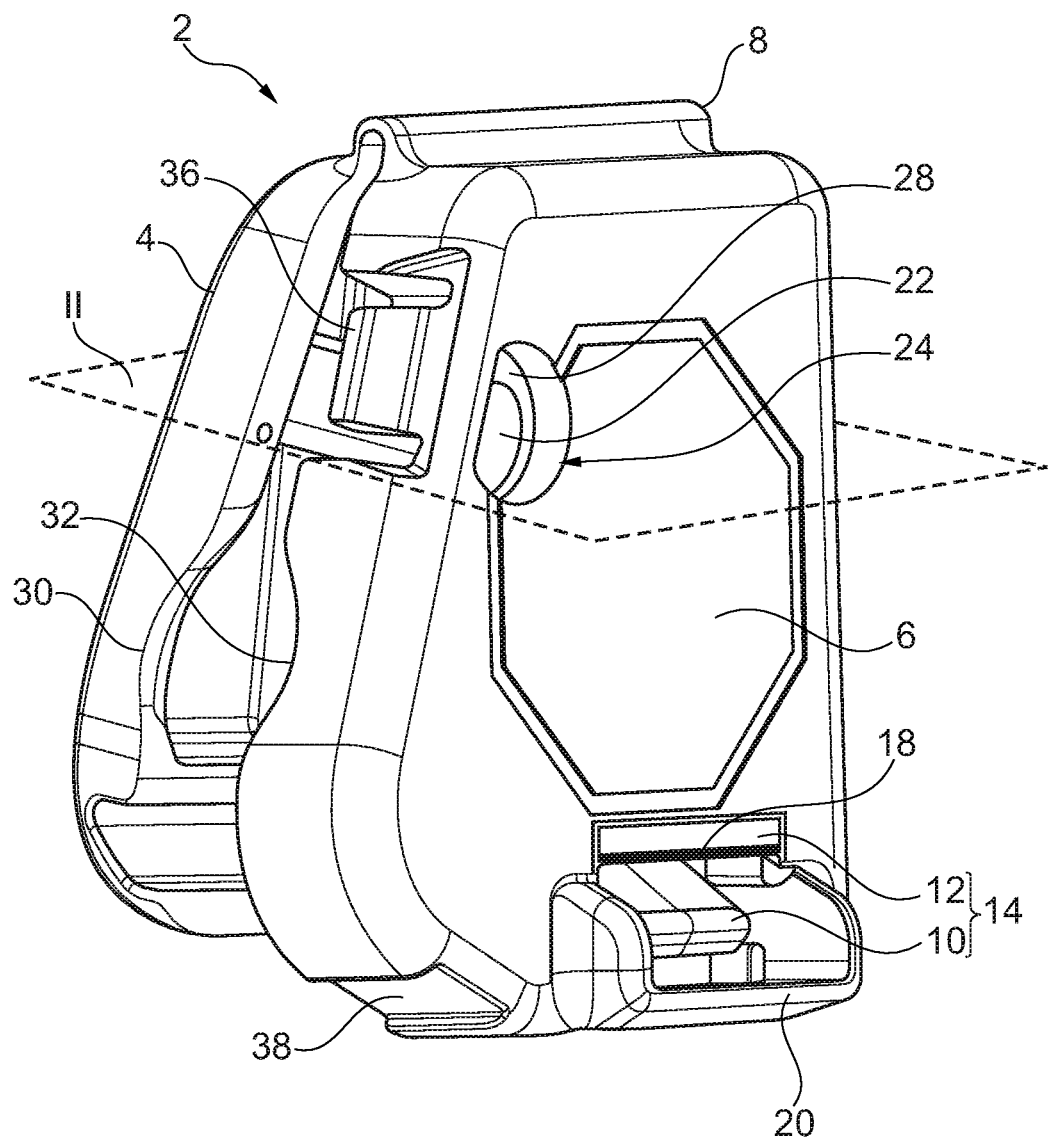
FIG. 1 shows a perspective view of a hose clamp according to a first embodiment in an opened position.

A first end of the first clamping portion 4 is provided with a hinge 8 by means of which the first clamping portion is pivotally connected to a first end of the second clamping portion 6.

The two clamping portions 4 and 6 may be made from a thermoplastic polymer and the hinge 8 as a film hinge may be made in one piece with the two clamping portions 4 and 6.

As an alternative, the hinge 8 could also be realized by means of protrusions which are provided on the first ends of the clamping portions 4 and 6 and engage each other in the manner of pinnacles, or implemented by means of a separately manufactured, attached hinge.

At a second end opposite to its first end, the first clamping portion 4 comprises a first spring clamp 10. At a second end opposite to its first end, the second clamping portion 6 comprises a first spring clamp seating 12. The first spring clamp 10 and the first spring clamp seating 12 together form a latching element 14.

The first spring clamp 10 extends from the second end of the first clamping portion 4 substantially perpendicular to the first clamping portion 4 toward the second clamping portion 6 and comprises a ramp-shaped free end. If the two clamping portions 4 and 6 are moved toward each other starting from an open position shown in FIG. 1, the two second ends of the clamping portions 4 and 6—as from a first closing angle enclosed between the clamping portions 4 and 6—cooperate such that the first spring clamp 10 is swiveled in a first swiveling direction by means of its ramp-shaped free end by the first spring clamp seating 12. As from a smaller, second closing angle, the first spring clamp 10 swivels back in a second swiveling direction opposite to the first swiveling direction and by means of an undercut 16 arranged behind the ramp-shaped free end brings about a positive form locking with the first spring clamp seating 12.

Figure 3:
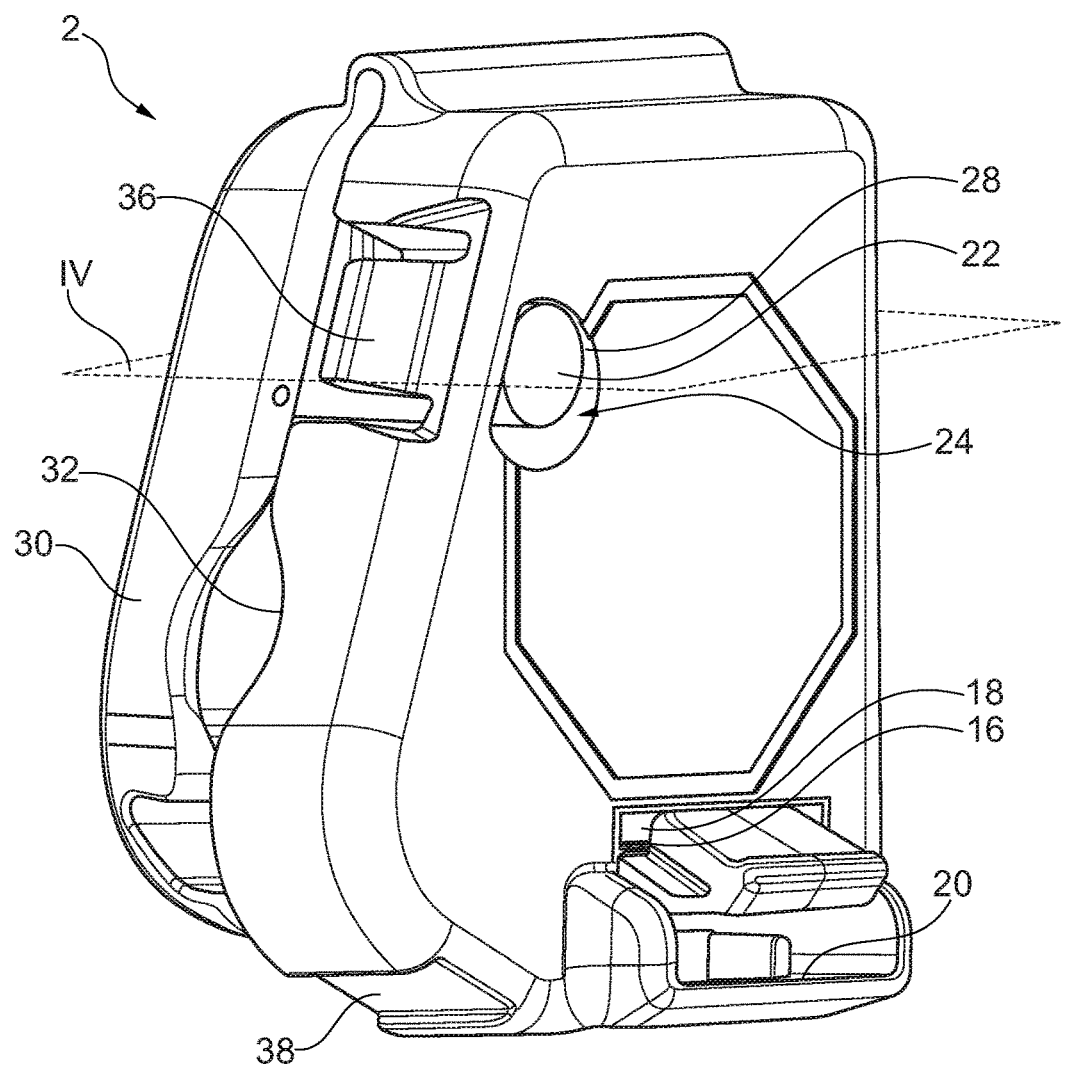
FIG. 3 shows a perspective view of the hose clamp shown in FIG. 1 in a closed position.

If the two second ends of the clamping portions 4 and 6 are connected to each other through the positive form locking, the hose clamp 2 is in a closed position shown in FIG. 3 and the two clamping portions 4 and 6 are in a closed relative position.

In order to release the positive form locking between the two second ends of the two clamping portions 4 and 6, the first spring clamp 10 has to be moved in the first swiveling direction, so that the undercut 16 on the first spring clamp 10 is disengaged from the first spring clamp seating 12.

The first spring clamp seating 12 is realized by means of a through-hole provided on the second end of the second clamping portion 6 and extending substantially perpendicular to the second clamping portion, comprising an edge 18 which can cooperate with the undercut 16 in a form-locking manner. At the side of the through-hole facing away from the first clamping portion 4, the rim of the through-hole is provided with an enclosure 20 which in the closed position of the hose clamp 2 shields the free end of the first spring clamp 12 from three sides and allows a lateral access to the first spring clamp 12 substantially only in the direction of the first swiveling direction.

The hinge 8 is designed such that it is tensioned in the closed position shown in FIG. 3 and not tensioned in the open position shown in FIG. 1. As an alternative, it would also be possible that the hinge 8 is not tensioned in the closed position of the hose clamp 2.

At a part of the first clamping portion 4 facing the first end of the first clamping portion 4, a feeler pin 22 is provided so as to extend substantially perpendicular to the first clamping portion 4 toward the second clamping portion 6.

At a part of the second clamping portion 6 facing the first end of the second clamping portion 6, a feeler pin seating 24 is provided so as to extend substantially perpendicular to the second clamping portion 6.

Figure 4:
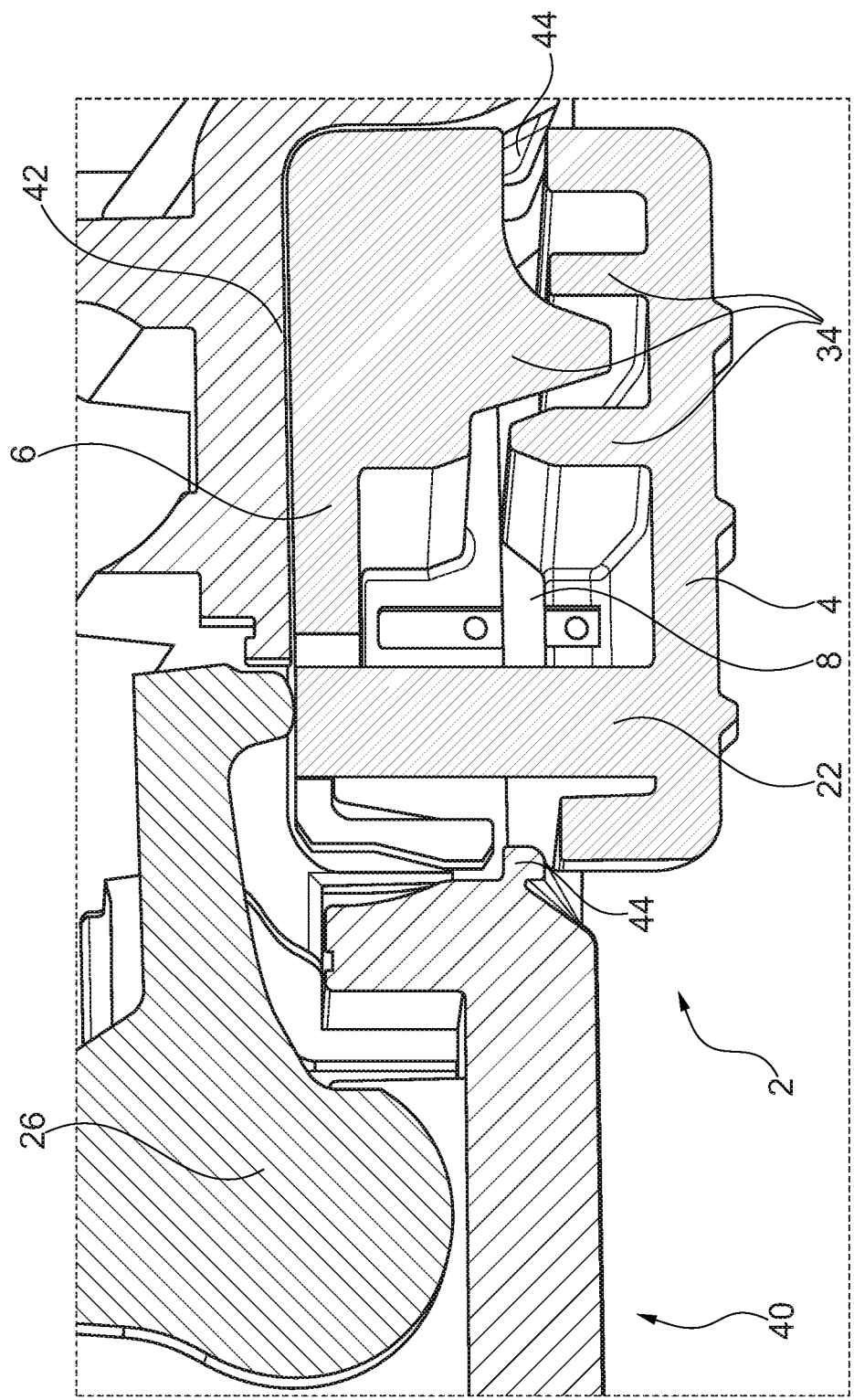
FIG. 4 shows a view of the section plane IV, indicated in FIG. 3, through the closed hose clamp in a state when mounted on the medical pump.

The circular cylindrical feeler pin 22 and the feeler pin seating 24 realized as a through-hole are dimensioned such that in the closed position of the hose clamp 2 the free end of the feeler pin 22 is situated at the side of the feeler pin seating 24 facing away from the first clamping portion 4, and the position of the free end of the feeler pin 22, as shown in FIG. 4, can be detected by means of a tactile sensor 26 which is arranged on the side of the second clamping portion 6 facing away from the first clamping portion 4.

To be more precise, the feeler pin 22 is a protrusion in the form of a circular cylinder whose free end in the closed position of the hose clamp 2 is located within the feeler pin seating 24 in the form of a largely circular through-hole; here, a surface of the free end facing away from the first clamping portion 4 is coplanar (at least in sections) with the outer surface of the side of the second clamping portion 6 facing away from the first clamping portion 4 (see FIGS. 3 and 4). In the closed position, the free end of the feeler pin 22 is arranged so as to be preferably off-center relative to the feeler pin seating 24 (i.e. a gap 28 between the outer surface of the free end of the feeler pin 22 and the inner surface of the feeler pin seating 24 is smaller at the side of the feeler pin seating 24 facing the hinge 8 than at the side facing the latching element 14).

Figure 2:
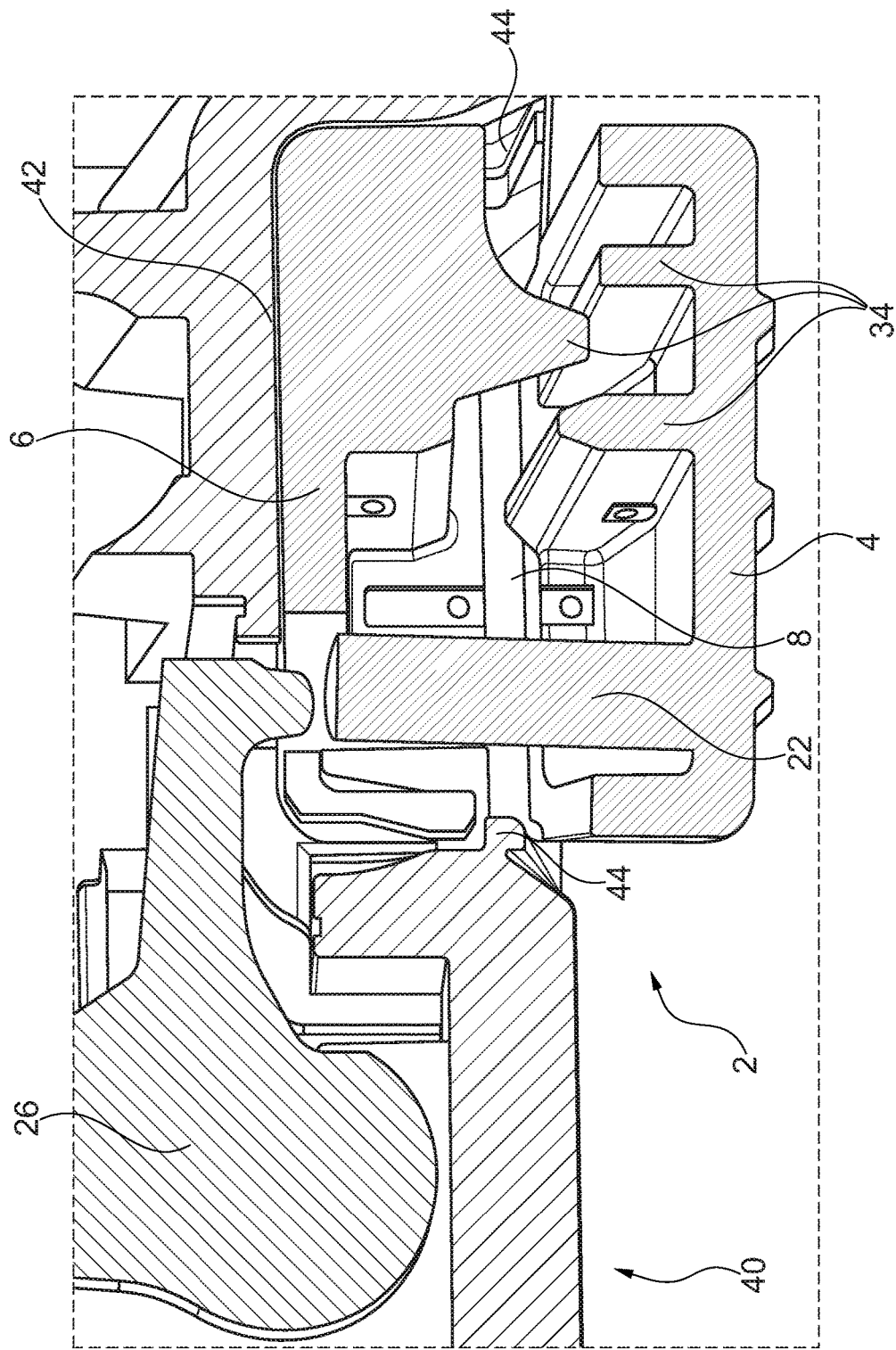
FIG. 2 shows a view of the section plane H, indicated in FIG. 1, through the opened hose clamp in a state when mounted on a medical pump.

If the hose clamp is in the open position shown in FIGS. 1 and 2, the free end of the feeler pin 22 is spaced—in the axial direction of the feeler pin 22 or the feeler pin seating 24—from the outer surface of the side of the second clamping portion 6 facing away from the first clamping portion 4, and the gap 28 on the side of the feeler pin seating 24 facing the hinge 8 is larger than on the side facing the latching element 14.

A first, preferably chute-like hose seating 30 is provided on the first clamping portion 4 between the feeler pin 22 and the first spring clamp 10.

A second, preferably chute-like hose seating 32 is provided on the second clamping portion 6 between the feeler pin seating 24 and the first spring clamp seating 12.

The two hose seatings 30 and 32 are formed such that they are in contact at least in sections with a hose arranged between the clamping portions 4 and 6, if the clamping portions 4 and 6 are moved to the closed relative position.

As shown in FIGS. 2 and 4, clamping ribs 34 are provided on the clamping portions 4 and 6 so as to extend perpendicular to the hinge axis and transverse to the hose seatings 30 and 32; in the closed position of the hose clamp 2, said clamping ribs exert a local pressure on the hose which is received in the hose seatings 30 and 32 and is flexible at least in this area, so that the hose is compressed and the interior of the hose is blocked in the area of the clamping ribs 34. The clamping ribs 34 may be arranged in such a manner that they do not only extend in a direction perpendicular to the hinge axis, but also in a direction parallel to the hinge axis between the feeler pin 22 or feeler pin seating 24 and the latching element 14.

At least a second spring clamp 36 and at least a second spring clamp seating 38 are provided on the lateral borders of the second clamping portion 6.

If the hose clamp 2 is attached to a medical pump 40, the second clamping portion 6 is received in a pump-side clamping portion seating 42 whose outline is equal to the outline of the second clamping portion 6. The connection between the hose clamp 2 and the pump 40 is ensured by a form-fitting cooperation between protrusions 44 or spring clamps at the rim of the clamping portion seating 42 and the second spring clamp 36 and/or the second spring clamp seating 38.

As shown in FIG. 2, the tactile sensor 26 is designed such that a feeler 46 of the tactile sensor 26 protrudes from the side facing away from the first clamping portion 4 into the feeler pin seating 24 of the opened hose clamp 2 attached to the pump 40. If the hose clamp 2 mounted on the pump 40 is closed, the feeler 46 is displaced by the feeler pin 22 of the first clamping portion 2 out of the feeler pin seating 24 (see FIG. 4). Depending on how far the feeler 46 is moved out of the feeler pin seating 24, the tactile sensor 24 forwards a signal (0 or 1) to a (not shown) electronic control unit in the pump 40 which corresponds to the degree of openness of the two clamping portions 4 and 6.

Figure 5:
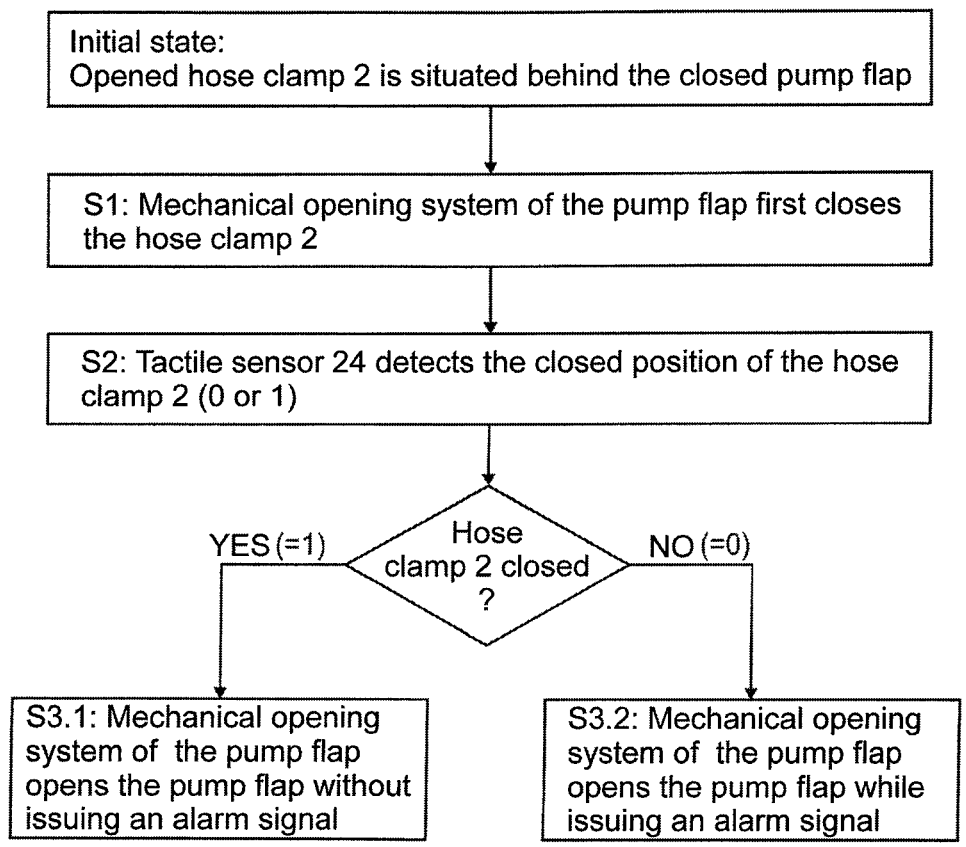
FIG. 5 shows a flow diagram of a pump flap opening procedure.
Figure 6:
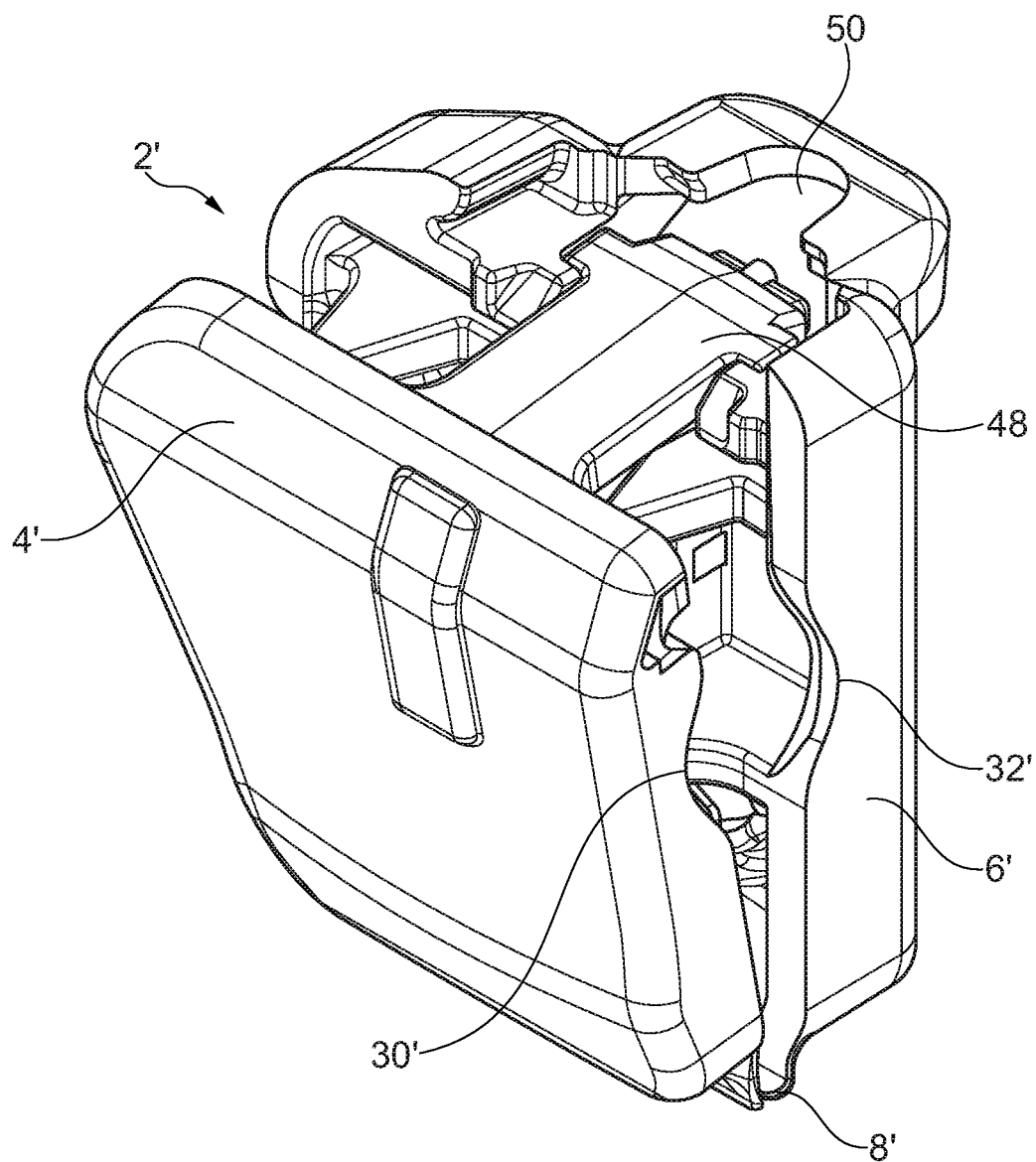
FIG. 6 shows a perspective view of a hose clamp according to a second embodiment in an opened position.
Figure 7A:
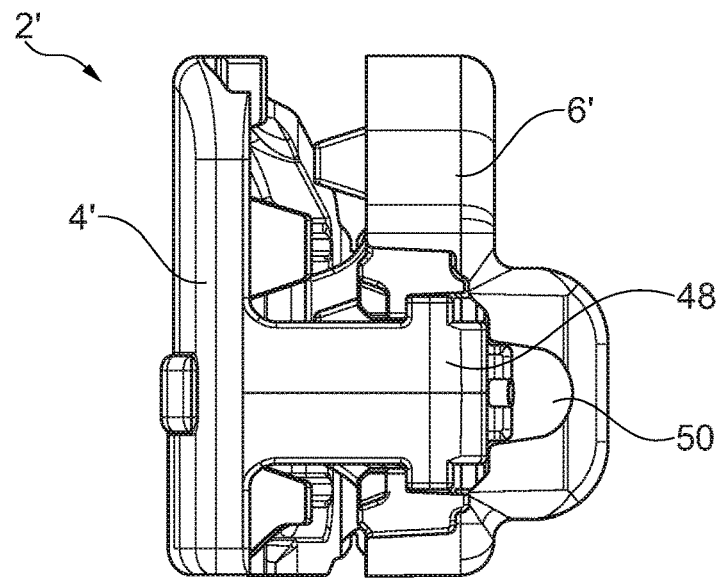
FIG. 7A shows a top view of the hose clamp shown in FIG. 6.
Figure 7B:
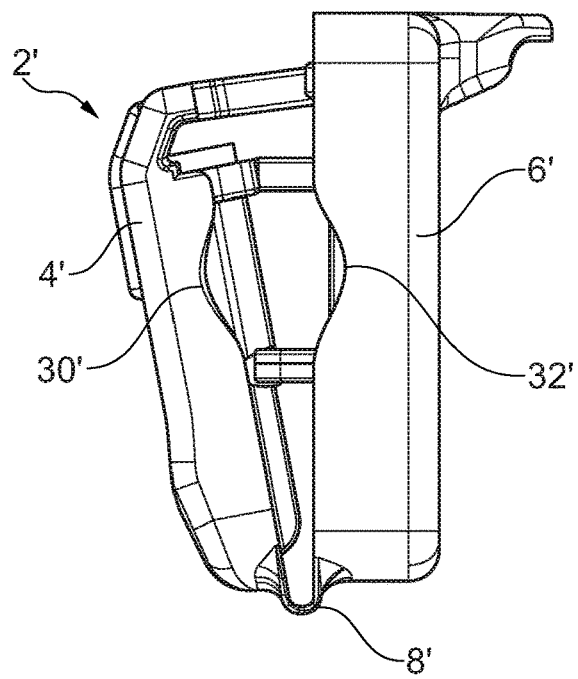
FIG. 7B shows a side view of the hose clamp shown in FIG. 6.

FIG. 5 illustrates an exemplary pump flap opening procedure. If the pump 40 is in an operable state in which a hose is connected to the pump 40 and secured by means of the hose clamp 2, the opened hose clamp is situated behind the closed pump flap (see initial state in FIG. 5).

If a mechanical opening system of the pump flap is actuated (see step S1 in FIG. 5), the mechanical opening system of the pump flap first closes the hose clamp 2 by acting upon the latching element 14 of the hose clamp 2.

If the tactile sensor 26 detects that the hose clamp 2 is properly closed (see step S2 in FIG. 5), the actual process of opening the pump flap by means of the mechanical opening system will not result in issuing an alarm signal (see step S3.1 in FIG. 5).

If the tactile sensor 26 detects that the hose clamp 2 is not properly closed (see step S2 in FIG. 5), the actual process of opening the pump flap by means of the mechanical opening system results in issuing an alarm signal (see step S3.2 in FIG. 5).

Said alarm signal can be realized by means of a visual indication (e.g. a flashlight) and/or a loudspeaker.

The mechanical opening system of the pump flap may be designed such that the process of opening the pump flap also results in the pump being switched off.

A hose clamp 2' according to a second embodiment of the invention is shown in FIGS. 6 to 11. The hose clamp 2' also comprises two clamping portions 4' and 6' which are connected to each other via a film hinge 8'.

At the end of the first clamping portion 4' facing away from the film hinge 8', a covering portion 48 is provided which in the closed relative position of the two clamping portions 4' and 6' extends toward the second clamping portion 6'.

At the end of the second clamping portion 6' facing away from the film hinge 8', an aperture 50 is provided which in the closed relative position of the two clamping portions 4' and 6' is concealed by the covering portion. In this context, "concealed" means that a light beam extending parallel to the main direction of extension of the second clamping portion 6' goes through the aperture 50 if the hose clamp 2' is open (see FIGS. 7A and 8) and hits the covering portion 50 if the hose clamp 2' is closed (see FIGS. 10A and 11).

Just like the hose clamp 2 according to the first embodiment, the hose clamp 2' according to the second embodiment also comprises a first hose seating 30' in the form of a chute-like recess (see FIGS. 6, 7B, 9 and 10B) at its first clamping portion 4' between its end facing the film hinge 8' and its end facing away from the film hinge 8', and comprises a second hose seating 32' in the form of a chute-like recess (see FIGS. 6, 7B, 9 and 10B) at its second clamping portion 6' between its end facing the film hinge 8' and its end facing away from the film hinge 8'.

Figure 8:
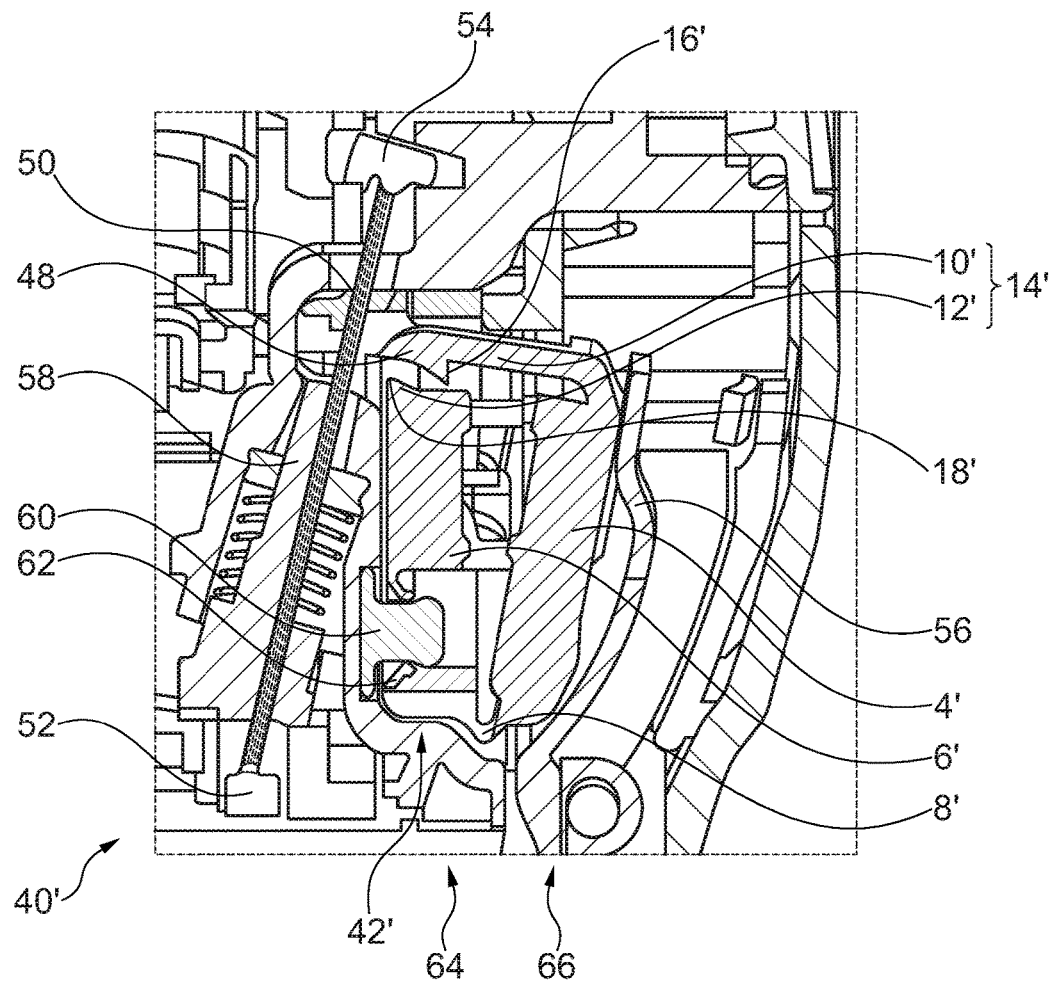
FIG. 8 shows a view of the opened hose clamp shown in FIG. 6 in a state when mounted on a medical pump.
Figure 9:
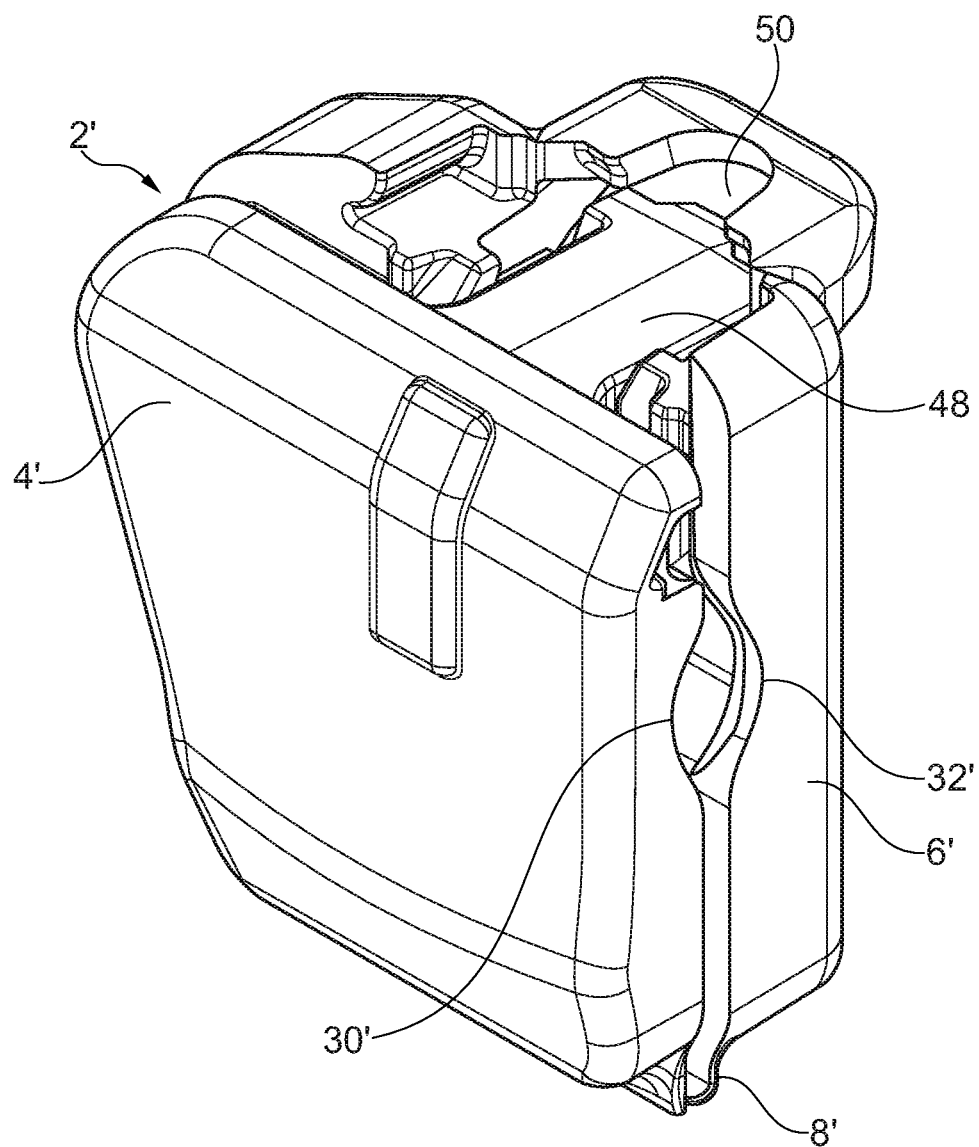
FIG. 9 shows a perspective view of the hose clamp shown in FIG. 6 in a closed position.
Figure 10A:
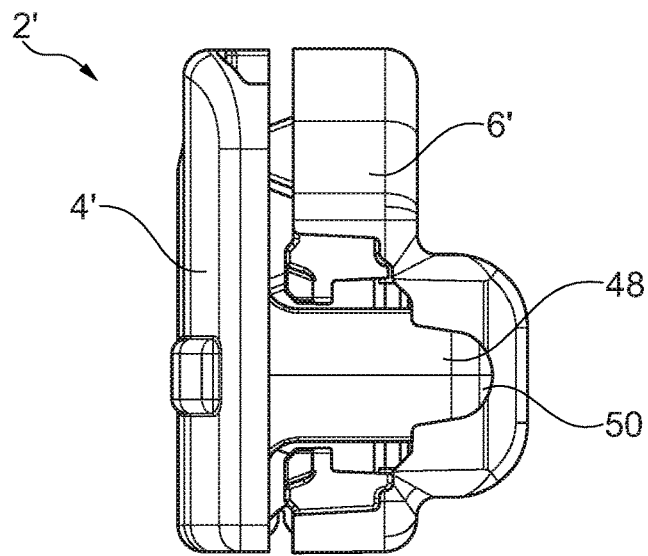
FIG. 10A shows a top view of the hose clamp shown in FIG. 9.
Figure 10B:
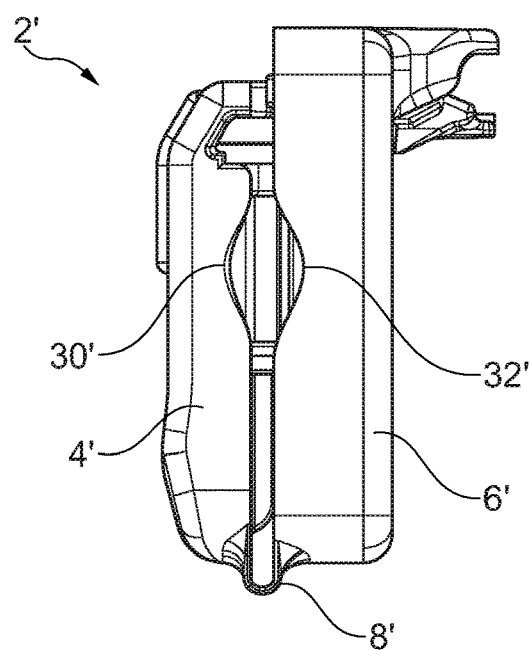
FIG. 10B shows a side view of the hose clamp shown in FIG. 9.
Figure 11:
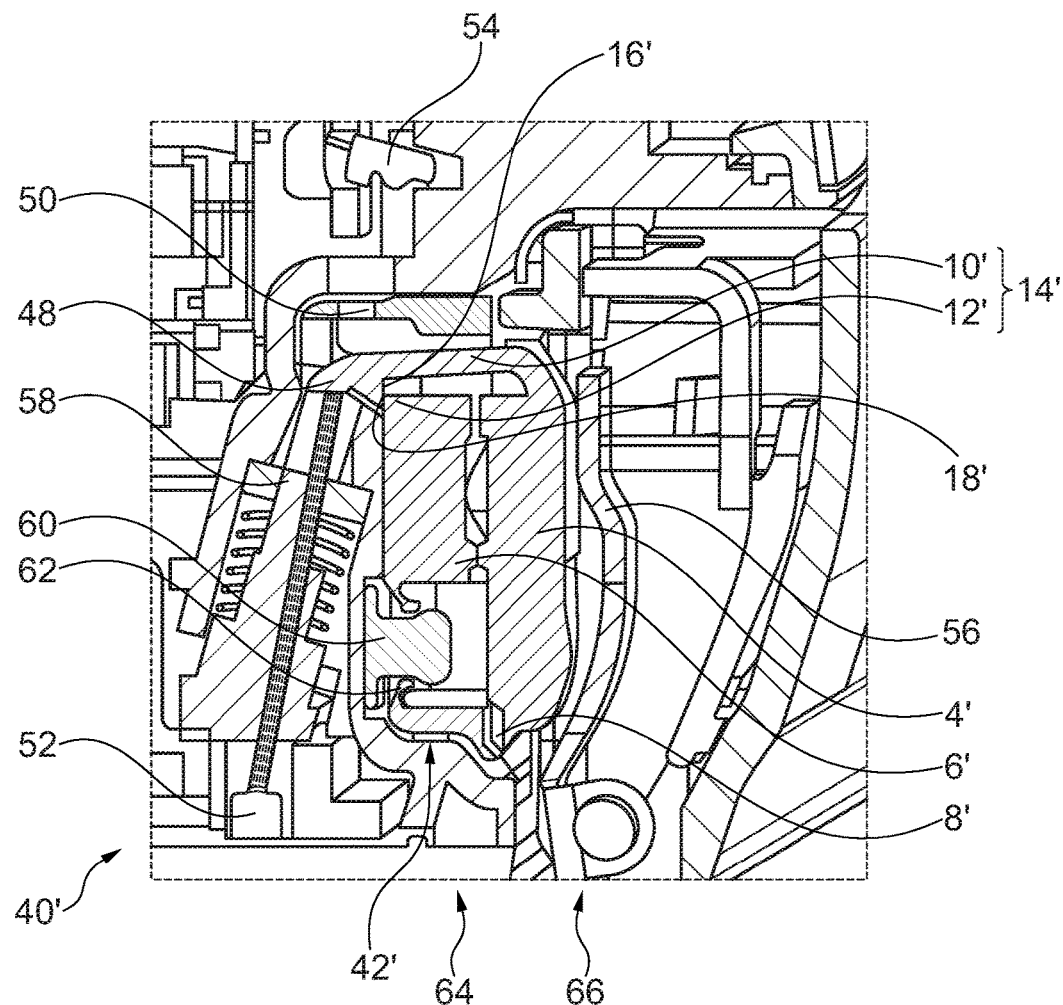
FIG. 11 shows a view of the hose clamp shown in FIG. 9 in a state when mounted on a medical pump.

As shown in FIGS. 8 and 11, the covering portion 48 is formed by a first spring clamp 10' which together with a first spring clamp seating 12' forms a latching element 14'. In terms of its latching function, the latching element 14' according to the second embodiment corresponds to the latching element 14 according to the first embodiment. Here, the first spring clamp 10' is provided with an undercut 16' which cooperates in a form-fitting manner with an edge 18' on the first spring clamp seating 12' if the hose clamp 2' is closed.

In FIG. 8, the hose clamp 2' received in a hose clamp seating 42' is shown in an opened state. The hose clamp seating 42' is provided on a main body 64 of a pump 40' and is covered by a pump flap 66 attached on the main body 64, if the pump flap 66 as shown in FIGS. 8 and 11 is in a closed position. A snap fastener or clip 60 in the form of a harbor bitt is provided in the hose clamp seating 42' and cooperates in a form-fitting manner with a clip seating 62 in the second clamping portion 6' if the hose clamp 2' is received in the hose clamp seating 42'. The clip seating 62 has the shape of a round opening whose rim or whose spring lugs can be elastically expanded allowing many insertion and removal processes.

Provided in the pump flap 66 is a first actuator element 56 in the form of a swiveling lever whose pivot axis extends substantially parallel to the hinge axis of the film hinge 8'. By means of the first actuator element 56, the first clamping portion 4' can be swiveled from an opened relative position toward the second clamping portion 6' into a closed relative position.

Provided in the main body 64 is a second actuator element 58 in the form of a linearly displaceable bolt whose direction of displacement extends transverse to the first spring clamp 10'. In the closed relative position of the two clamping portions 4' and 6', the second actuator element 58 is capable of moving the first spring clamp 10' such that the undercut 16' on the first spring clamp 10' on the first clamping portion 4' can be disengaged from the edge 18' on the first spring clamp seating 12' on the second clamping portion 6'. If the undercut 16' and the edge 18' are disengaged, the first clamping portion 4' moves to the opened relative position as soon as there is a certain minimum pressure in the hose clamped by the hose clamp 2'. As an alternative, the hose clamp 2' may also be designed such that the clamping portions 4' and 6' are in a tension-free state in the opened relative position.

In the main body 64, a light source 52 is provided at one side of the end of the second clamping portion 6' facing away from the film hinge 8', and at the other side of said end a light sensor 54 is provided. In the context of this description and the claims, the term 'light' is to be understood as any electromagnetic radiation which can be shielded by means of plastic or metallized plastic. Thus, the light sensor 54 is generally distinguished in that it is able to detect at least a change in properties or a property of the light, such as the intensity, for example. The light source 52 and the light sensor 54 are arranged in the main body 64 such that a light beam can radiate from the light source 52 through the aperture 50 to the light sensor 54, if the clamping portions 4' and 6' are in the opened relative position, and that a light beam from the light source 52 hits the covering portion 48 and cannot radiate up to the light sensor 54 if the clamping portions 4' and 6' are in the closed relative position.

The embodiments of the hose clamp according to aspects of the invention and of the medical pump according to aspects of the invention which are shown in FIGS. 1 to 11 and have been described above merely represent one possible implementation of the claimed invention.

By way of example, the feeler pin 22 does not necessarily have a circularly cylindrical shape, but may be generally cylindrical or shaped like a rotation body. Accordingly, the cross-section of the feeler pin seating 24 may be polygonal or oval.

The hose clamp 2 is made in one piece. As an alternative, it is also possible to manufacture the hose clamp 2 by assembling a plurality of individual parts.

In the embodiment as described, the degree of openness of the hose clamp 2 is detected on the basis of the displacement of the feeler 46 in the axial direction of the feeler pin seating 24. As an alternative or in addition, it would be possible to use the feeler 46 for detecting the displacement of the feeler pin 22 relative to the feeler pin seating 24 transverse to the axial direction of the feeler pin seating 24 (determining the width of the gap 28).

The invention claimed is:

1. A medical pump for conveying a medium, the medical pump comprising:
   a seating for a hose clamp which is separate from the medical pump and arranged on a hose that is flexible at least in sections, said hose clamp comprising two clamping portions separated by a hinge defining an axis, wherein the two clamping portions are configured to move relative to each other pivotally around the axis defined by the hinge, and the hose is arranged between the two clamping portions parallel to the axis defined by the hinge; and wherein the two clamping portions are configured to be brought into a closed relative position with respect to each other, in which the hose arranged between the two clamping portions is pinched off such that no medium can flow through an interior of the hose, and into an opened relative position with respect to each other, in which the hose arranged between the two clamping portions is not pinched off, so that a medium can flow through the interior of the hose;
   a sensor provided in the seating, the sensor configured to detect whether the two clamping portions are in the closed or the opened relative position when the hose clamp is provided in the seating; and
   a pump flap which in a closed position covers the seating such that the hose clamp at least one of cannot be removed from the seating or cannot be inserted into the seating, and in an opened position releases the seating such that the hose clamp at least one of can be removed from the seating or can be inserted into the seating.

2. The medical pump according to claim 1, further comprising:
   an electronic data processing unit configured to at least one of detect structural integrity or functional integrity of the hose clamp received in the seating required for use of the hose clamp with the aid of a temporal course of a measurement carried out by the sensor during the transition of the two clamping portions from the closed to the opened relative position or from the opened to the closed relative position.

3. The medical pump according to claim 1, further comprising:
   an actuator configured to move the two clamping portions of the hose clamp received in the seating at least one of from the closed to the opened or from the opened to the closed relative position.

4. The medical pump according to claim 1, further comprising:
   an actuator configured to move the two clamping portions of the hose clamp received in the seating at least one of from the closed to the opened or from the opened to the closed relative position, wherein the actuator, in the closed position of the pump flap, is configured to move the two clamping portions of the hose clamp when received in the seating at least one of from the closed to the opened or from the opened to the closed relative position.

5. The medical pump according to claim 3, wherein the opened relative position of the two clamping portions of the hose clamp received in the seating can be altered by the actuator such that a degree of openness of the interior of the hose and hence a volumetric flow of the medium flowing through the hose can be adjusted.

6. The medical pump according to claim 5, wherein the sensor is configured to detect the alteration of the opened relative position of the two clamping portions of the hose clamp received in the seating, so that the degree of openness of the interior of the hose and hence the volumetric flow of the medium flowing through the hose can be detected.

7. The medical pump according to claim 1, wherein the sensor detects the closed relative position of the two clamping portions by sensing the position of a first one of the two clamping portions, and the seating is configured such that a second one of the two clamping portions is fixed.

8. The medical pump according to claim 1, further comprising:
a main body relative to which the pump flap can be moved;
wherein the seating is provided on the main body; and
wherein a first of the two clamping portions is moved by the pump flap.

9. The medical pump according to claim 1, further comprising:
a light source arranged on the medical pump;
wherein the sensor is a light sensor responsive to at least one of the two clamping portions at least one of interrupting, changing or deflecting a light beam emitted from the light source.

10. The medical pump according to claim 1, wherein the sensor is a tactile sensor responsive to contact of the sensor with at least one of the two clamping portions.

11. The medical pump according to claim 1, further comprising:
a snap fastener or clip provided in the seating for detachable fixation by cooperating in a form-locking manner with a clip seating formed in one of the two clamping portions when the hose clamp is received in the seating.

12. A medical system comprising a medical pump according claim 1.

13. A system comprising:
a hose clamp arranged on a hose that is flexible at least in sections, said hose clamp comprising two clamping portions separated by a hinge defining an axis, wherein the two clamping members are movable relative to each other pivotally around the axis defined by the hinge, and the hose is arranged between the two clamping portions parallel to the axis defined by the hinge; and
wherein the two clamping portions can be brought into a closed relative position with respect to each other in which a hose arranged between the two clamping portions is pinched off such that no medium can flow through an interior of the hose and to an opened relative position in which a medium can flow through the interior of the hose, and into an opened relative position with respect to each other, in which the hose arranged between the two clamping portions is not pinched off, so that a medium can flow through the interior of the hose; and
a medical pump for conveying a medium, the medical pump comprising:
a seating for the hose clamp which is separate from the medical pump, and
a sensor provided in the seating, the sensor configured to detect whether the two clamping portions are in the closed or the opened relative position when the hose clamp is provided in the seating; and
wherein at least one of the two clamping portions is configured to connect to the medical pump at the seating for the hose clamp; and
wherein a first one of the two clamping portions comprises a portion which covers an aperture provided on a second one of the two clamping portions in a closed relative position of the two clamping portions and at least partially exposes said aperture in the opened relative position of the two clamping portions.

14. A medical system comprising a system according to claim 13.

15. A system comprising:
a hose clamp arranged on a hose that is flexible at least in sections, said hose clamp comprising:
two clamping portions movable relative to each other, wherein the two clamping portions can be brought into a closed relative position with respect to each other, in which closed relative position the hose arranged between the two clamping portions is pinched off such that no medium can flow through an interior of the hose, and into an opened relative position with respect to each other, in which the hose arranged between the two clamping portions is not pinched off, so that a medium can flow through the interior of the hose;
a latching element configured to fix the two clamping portions in the closed relative position; and
a protrusion provided on a first one of the two clamping portions; and
a medical pump for conveying a medium, the medical pump comprising:
a seating for the hose clamp which is separate from the medical pump, and
a sensor provided in the seating, the sensor configured to detect whether the two clamping portions are in the closed or the opened relative position when the hose clamp is provided in the seating;
wherein at least one of the two clamping portions is configured to connect to the medical pump at the seating for the hose clamp; and
wherein the protrusion in the closed relative position protrudes toward a second of the two clamping portions such that it extends up to a rear side of the second clamping portion facing away from the first clamping portion, and the closed relative position of the two clamping portions of the hose clamp connected to the medical pump can be sensed by the sensor arranged on the rear side of the second clamping portion on the medical pump.

16. The system according to claim 15, wherein the protrusion extends through a continuous recess in the second clamping portion in the closed relative position.

17. The system according to claim 15, wherein the two clamping portions are pivotally connected to each other by a hinge, the latching element is arranged on each of the two clamping portions on a side facing away from the hinge,
a hose seating is provided between the side facing the latching element and the side facing the hinge of each clamping portion, and
the recess and the protrusion are each arranged between the hinge and the respective hose seating of the corresponding clamping portion.

* * * * *